United States Patent [19]

Lodge et al.

[11] Patent Number: 5,026,904

[45] Date of Patent: Jun. 25, 1991

[54] PRODUCTION OF HYDROCARBYL FORMATES

[75] Inventors: Philip G. Lodge, Staines; David J. H. Smith, Camberley, both of England

[73] Assignee: The British Petroleum Company p.l.c., London, England

[21] Appl. No.: 701,796

[22] Filed: Feb. 15, 1985

Related U.S. Application Data

[63] Continuation of Ser. No. 491,582, May 4, 1983, abandoned.

[30] Foreign Application Priority Data

May 15, 1982 [GB] United Kingdom ............... 8214203

[51] Int. Cl.$^5$ ............................................. C07C 51/12
[52] U.S. Cl. ..................................... 560/232; 560/265
[58] Field of Search ................................ 560/232, 265

[56] References Cited

U.S. PATENT DOCUMENTS

| | | | |
|---|---|---|---|
| 3,317,593 | 5/1967 | Enk et al. | 562/609 |
| 4,299,981 | 11/1981 | Leonard | 562/609 |

FOREIGN PATENT DOCUMENTS

| | | | |
|---|---|---|---|
| 422500 | 12/1925 | Fed. Rep. of Germany | 562/609 |
| 5346820 | 11/1976 | Japan . | |
| 53-46816 | 1/1978 | Japan . | |

*Primary Examiner*—Jose G. Dees
*Attorney, Agent, or Firm*—Brooks Haidt Haffner & Delahunty

[57] ABSTRACT

Hydrocarbyl formates, convertible by hydrolysis into formic acid, are produced by reacting carbon dioxide and hydrogen with a compound of formula ROH wherein R is a hydrocarbyl group in the presence of a substantially insoluble compound of an element selected from Groups III to VIII of the Periodic Table, which element exhibits amphoteric or basic properties, and as catalyst a compound of a transition metal of Group VIa, VIIa or VIII of the Periodic Table, particularly rhodium, ruthenium or iridium.

10 Claims, No Drawings

PRODUCTION OF HYDROCARBYL FORMATES

This application is a continuation of U.S. application Ser. No. 491,582, filed May 4, 1983 abandoned.

The present invention relates to a process for the production of hydrocarbyl formates by reacting carbon dioxide, hydrogen and an alcohol in the presence of a catalyst.

Japanese patent publication No 53-46820 describes a process for the production of formic acid and its esters by reacting a compound of formula ROH (wherein R is either hydrogen or a hydrocarbyl group) with carbon dioxide and hydrogen in the presence as catalyst of low valent and/or hydride complexes of Group VIII transition metals and basic materials. The specification teaches that using water as the compound of formula ROH the product is formic acid and using an alkanol as the compound ROH the product is an alkyl ester of formic acid. Basic materials which are used in the process of the invention are said to be the compounds consisting of alkali or alkaline earth metals, for example, Li, Na, K, Mg, Ca, Sr, in the form of hydroxides, carbonates, bicarbonates, or alcoholates. Specific basic materials which may be used are LiOH, KOH, NaOH, $Mg(OH)_2$, $Ca(OH)_2$, $Li_2CO_3$, $Na_2CO_3$, $K_2CO_3$, $MgCO_3$, $SrCO_3$, $LiHCO_3$, $NaHCO_3$, $KHCO_3$, $MgK(HCO_3)_3$, $KOCH_3$, $KOC_2H_5$, $NaOCH_3$, $NaOC_2H_5$ and $Mg(OCH_3)_2$.

Japanese patent publication No 53-46816 describes the production of formic acid and its esters by a similar process to that described in publication No 53-46820, except that instead of an inorganic base there is used an organic base which is an aliphatic tertiary amine.

We have found that in addition to formic acid esters, the process of Japanese patent publication No 53-46820 produces formate salts of the alkali or alkaline earth metal employed as the base. The selectivity to the desired formic acid ester is thereby reduced, as is the overall yield of the ester. We have found that the production of by-products such as the formate salts can be substantially eliminated and the overall yield of formate esters improved by using, instead of the alkali or alkaline earth metal base, a substantially insoluble compound of an element selected from Groups III to VIII of the Periodic Table, which element exhibits amphoteric or basic properties.

Accordingly the present invention is a process for the production of a hydrocarbyl formate which process comprises reacting carbon dioxide and hydrogen with a compound of formula ROH wherein R is a hydrocarbyl group in the presence of a substantially insoluble compound of an element selected from Groups III to VIII of the Periodic Table, which element exhibits amphoteric or basic properties, and as catalyst a compound of a transition metal of Group VIa, VIIa or VIII of the Periodic Table.

The Periodic Table referred to throughout this specification is the Periodic Table as found in Advanced Inorganic Chemistry by Cotton and Wilkinson, published by John Wiley & Sons, Fourth Edition.

Both carbon dioxide and hydrogen are widely available on a commercial scale. Carbon dioxide may be added as a gas or as a solid, preferably as a gas. Hydrogen is added as a gas. High partial pressures of carbon dioxide and hydrogen are preferred. The total pressure may suitably be a pressure up to 200 bars. It is preferred that the partial pressure of hydrogen be greater than the partial pressure of carbon dioxide.

The hydrocarbyl substituent R in the compound of formula ROH may suitably be an alkyl, cycloalkyl or aryl group, preferably an alkyl group and more preferably a lower alkyl group, eg a $C_1$ to $C_4$ alkyl group. Thus the compound of formula ROH may be methanol, ethanol, a propanol or a butanol. Mixtures of compounds having the formula ROH may be used if so desired.

Elements which exhibit amphoteric character in their compounds generally are to be found in Groups IIIb, IVb and Vb of the Periodic Table and include aluminium, tin, gallium and antimony. Titanium also exhibits amphoteric character. Elements which exhibit basic properties in their compounds include for example the rare earth elements and certain transition metals, for example manganese and zirconium, and certain other metals from Groups IIIb, IVb and Vb of the Periodic Table, for example bismuth and lead. Preferably the particular compound of the element employed is the oxide. Suitable compounds include alumina, for example a Woelm alumina, lanthanum oxide, titania, zirconia, gallia, lead oxide and zinc oxide. The base may suitably be employed in either particulate or granular form. It is preferred to dry the base prior to its addition to the reactants, though the presence of water can be tolerated. Drying may be accomplished by conventional means. Large amounts of the base are not essential to the performance of the invention and it is an advantage of the invention that the base suffers no substantial deactivation during the course of the reaction, ie it can be re-used in successive batch reactions. A further advantage of the use of bases embraced by the present invention is that being substantially insoluble in the reaction medium they facilitate product separation.

As catalyst there is used a compound of a transition metal of Group VIa, VIIa or VIII of the Periodic Table. Examples of suitable transition metals are manganese, rhenium, ruthenium, rhodium, palladium, osmium, iridium, platinum, chromium, molybdenum and tungsten, of which iridium, ruthenium and rhodium are preferred and ruthenium and rhodium are more preferred. Suitably the compound is a low-valent electron rich complex which may be added as such or in the form of a compound or compounds which give rise to such a complex under the reaction conditions. Thus the transition metal may suitably be added in the form of a salt, for example a halide, either alone or preferably together with a compound of formula $R^1R^2R^3X$, wherein X is phosphorus, arsenic or antimony, preferably phosphorus, and $R^1$, $R^2$ and $R^3$ are independently hydrocarbyl groups which may be alkyl, cycloalkyl, aryl or aralkyl groups, for example triphenyl phosphine. Alternatively, the transition metal may be added in the form of a complex wherein a ligand is the aforesaid compound of formula $R^1R^2R^3X$.

The process may suitably be carried out a temperature in the range 20° to 300° C., preferably in the range 75° to 150° C.

The process may be carried out batchwise or continuously, preferably continuously.

In a preferred embodiment the invention provides a process for the production of methyl formate which process comprises reacting gaseous carbon dioxide and hydrogen with methanol at a temperature in the range 20° to 300° C. and a combined pressure up to 200 bars in the presence of a substantially anhydrous Woelm alumina and as catalyst a compound of ruthenium.

Since the hydrocarbyl formate can be produced at high selectivity, its separation and recovery from the reaction mixture is considerably simplified. This may be effected for example by distillation.

The hydrocarbyl formate may be hydrolysed to produce formic acid, which is a desirable product having a number of applications, for example as an additive in silage production. The high selectivity to hydrocarbyl formates achievable by the process of the invention is again an advantage because the step of isolating reaction by-products prior to hydrolysis can be avoided.

In another aspect the invention provides a process for the production of formic acid which process comprises hydrolysing an hydrocarbyl formate produced by the process as hereinbefore described.

The hydrolysis may be accomplished by any of the many methods described in the literature, for example by the processes described in GB 1460491, U.S. Pat No. 4218568 and EP 5998.

The invention will now be described more particularly by reference to the following Examples. In the Examples product analyses were carried out by gas chromatography using a Pye Unicam 104 instrument with a column packed with PORAPAK Q.

EXAMPLE 1

To a 200 ml capacity stainless steel autoclave equipped with electrical heating and an electromagnetically driven vertical stirrer was charged $RuCl_2(PPh_3)_3$ (95.8 mg; 0.1 mmol); Woelm basic alumina, activity grade one (3.00 g; 0.0294 mol), tetrahydrofuran (3.97 g) and methanol (50 ml).

The autoclave was pressured to a steady-state 20 bar with $CO_2$ and then to a total pressure of 80 bar with $H_2$. The vessel was heated to 100° C. and held at this temperature for 16 hours. The autoclave was then allowed to cool to room temperature and the gases vented. 335 moles of methyl formate per mole of $RuCl_2(PPh_3)_3$ were obtained as the sole product.

EXAMPLE 2

The autoclave as used in Example 1 was charged with $RuCl_2(PPh_3)_3$ (97.3 mg; 0.102 mmol), Woelm basic alumina, activity grade one (3.00 g; 0.0294 mol), tetrahydrofuran (4.04 g) and methanol (50 ml).

The autoclave was pressured to a steady-state 20 bar with $CO_2$ and then to a total pressure of 80 bar with $H_2$. The vessel was heated to 100° C. and held at this temperature for 64 hours. The autoclave was then allowed to cool to room temperature and the gases vented. 470 moles of methyl formate per mole of $RuCl_2(PPh_3)_3$ were obtained as the sole product.

EXAMPLE 3

To a 300 ml capacity Hastelloy autoclave provided with electrical heating and an electromagnetically driven vertical stirrer was charged $RuCl_2(PPh_3)_3$ (97.8 mg; 0.102 mmol), Woelm basic alumina, activity grade one (3.0444 g; 0.0299 mol), tetrahydrofuran (4.05 g) and methanol (50 ml).

The autoclave was pressured to a steady-state 20 bar with $CO_2$ t- and then to a total pressure of 80 bar with $H_2$. The vessel was heated to 100° C. and held at this temperature for 12 hours. The autoclave was then allowed to cool to room temperature and the gases vented. 186 moles of methyl formate per mole of $RuCl_2(PPh_3)_3$ were obtained as the sole product.

EXAMPLES 4 to 6

The alumina was recovered from the reaction product of Example 3 and was used again in repeats of Example 3 with fresh $RuCl_2(PPh_3)_3$, liquid components and gaseous components over periods of 12 (Ex. 4), 5 (Ex. 5) and 5 (Ex. 6) hours. 231 (Ex. 4), 116 (Ex. 5) and 117 (Ex. 6) moles of methyl formate per mole of $RuCl_2(PPh_3)_3$ were obtained.

EXAMPLE 7

To the autoclave as used in Example 3 was charged $RuCl_2(PPh_3)_3$ (97.5 mg; 0.102 m mol), Woelm basic alumina, activity grade one (3.0212 g; 0.0296 mol), tetrahydrofuran (3.80 g) and ethanol (50 ml).

The autoclave was pressured to a steady-state 20 bar with $CO_2$ and then to a total pressure of 80 bar with $H_2$. The vessel was heated to 100° C. and held at this temperature for 5 hours. The autoclave was then allowed to cool to room temperature and the gases vented. 93 moles of ethyl formate per mole of $RuCl_2(PPh_3)_3$ were obtained as the sole product.

EXAMPLE 8

To the autoclave as used in Example 3 was charged $RuCl_2(PPh_3)_3$ (104.4 mg; 0.109 mmol), zinc oxide (Fisons Analytical Reagent) (2.3936 g; 0.0294 mol), tetrahydrofuran (4.02 g) and ethanol (50 ml).

The autoclave was pressured to a steady-state 20 bar with $CO_2$ and then to a total pressure of 80 bar with $H_2$. The vessel was heated to 100° C. and held at this temperature for 5½ hours. The autoclave was then allowed to cool to room temperature and the gases vented. 162 moles of ethyl formate per mole of $RuCl_2(PPh_3)_3$ were obtained as the sole product.

EXAMPLE 9

To the autoclave as used in Example 3 was charged $RuCl_2(PPh_3)_3$ (97.1 mg; 0.101 mmol), lead oxide (Ex. BDH, Analar Grade) (7.1042 g; 0.0297 mol), tetrahydrofuran (4.105 g) and methanol (50 ml).

The autoclave was pressured to a steady-state 20 bar with $CO_2$ and then to a total pressure of 80 bar with $H_2$. The vessel was heated to 100° C. and held at this temperature for 5 hours. The autoclave was then allowed to cool to room temperature and the gases vented. 127 moles of methyl formate per mole of $RuCl_2(PPh_3)_3$ were obtained as the sole product.

EXAMPLE 10

To a 150 ml stainless steel autoclave provided with electrical heating and a magnetically driven stirrer bar was charged $Ir(CO)Cl(PPh_3)_2$ (80.3 mg, 0.103 mmol), Woelm basic alumina, activity grade one (3.0013 g, 0.0294 mol) and methanol (30.05g).

The autoclave was pressured to a steady-state 15.8 bar with $CO_2$ and then to a total pressure of 62.1 bar with $H_2$. The vessel was heated to 100° C. and held at this temperature for 16 hours. The autoclave was then allowed to cool to room temperature and the gases vented. 10 moles of methyl formate per mole of $Ir(CO)Cl(PPh_3)_3$ were obtained as the sole product.

EXAMPLE 11

The autoclave as used in Example 10 was charged with $RhCl(PPh_3)_3$ (93.9 mg, 0.102 mmol), Woelm basic alumina, activity grade one (3.0049g, 0.0295 mol) and methanol (31.50g). The autoclave was pressured as in Example 10 with 15.5 bar of $CO_2$, then to a total pressure of 60.2 bar with $H_2$; it was then heated to 100° C. and held at this temperature for 16 hours. After cooling to room temperature and venting the gases, 77 moles of methyl formate per mole of $RhCl(PPh_3)_3$ were obtained as the sole product.

EXAMPLE 12

The autoclave as used in Example 10 was charged with $RuCl(eta^5-C_5H_5)(PPh_3)_2$ (73.5 mg, 0.101 mmol), Woelm basic alumina, activity grade one (3.0061g, 0.0295 mol) and methanol (31.18 g). The vessel was pressured as in Example 10 with 15.7 bar of $CO_2$, then to a total pressure of 61.9 bar with $H_2$; it was then heated to 100° C. and held at this temperature for 3 hours. After cooling to room temperature and venting the gases, 69 moles of methyl formate per mole of $RuCl(eta^5-C_5H_5)(PPh_3)_2$ were obtained as the sole product.

EXAMPLE 13

The autoclave as used in Example 10 was charged with $RuCl_2(PPh_3)_3$ (97.4 mg, 0.102 mmol), zinc oxide (Fisons, Analytical Reagent) (2.454 g, 0.0301 mol) and methanol (30.94 g). The vessel was pressured as in Example 10 with 15.6 bar of $CO_2$, then to a total pressure of 60.6 bar with $H_2$; it was then heated to 100° C. and held at this temperature for 3 hours. After cooling to room temperature and venting the gases, 106 moles of methyl formate per mole of $RuCl_2(PPh_3)_3$ were obtained as the sole product.

We claim:

1. A process for the production of a hydrocarbyl formate which process comprises reacting carbon dioxide and hydrogen with a compound of formula ROH wherein R is a hydrocarbyl group in the presence of a substantially insoluble compound of an element selected from Groups III to VIII of the Periodic Table which element exhibits amphoteric or basic properties, and as catalyst a compound of a transition metal of Group VIa, VIIa or VIII of the Periodic Table.

2. A process according to claim 1 wherein the compound of formula ROH is methanol, ethanol, a propanol or a butanol.

3. A process according to claim 1 wherein the substantially insoluble compound is a compound of are element of Group IIIb, IVb or Vb of the Periodic Table, which exhibits amphoteric properties, or titanium.

4. A process according to claim 1 wherein the substantially insoluble compound is a compound of a rare earth element, a transition metal element or an element of Groups IIIb, IVb or Vb of the Periodic Table, which element exhibits basic properties.

5. A process according to claim 1 wherein the substantially insoluble compound is a Woelm alumina, lanthanum oxide, titania, zirconia, gallia lead oxide or zinc oxide.

6. A process according to claim 1 wherein the catalyst is a compound of ruthenium, rhodium or iridium.

7. A process according to claim 1 wherein the catalyst is added in the form of a complex in which the ligand is a compound of formula $R^1R^2R^3X$ wherein X is phosphorus, arsenic or antimony and $R^1$, $R^2$ and $R^3$ are independently hydrocarbyl groups.

8. A process according to claim 1 wherein there is independently added a compound of formula $R^1R^2R^3X$ wherein X is phosphorus, arsenic or antimony and $R^1$, $R^2$ and $R^3$ are independently hydrocarbyl groups.

9. A process for the production of formic acid which process comprises hydrolysing an hydrocarbyl formate as obtained by the process as claimed in claim 1.

10. A process for the production of methyl formate which process comprises reacting gaseous carbon dioxide and hydrogen with methanol at a temperature in the range 20° to 300° C. and a combined pressure up to 200 bars in the presence of a substantially anhydrous Woelm alumina and as catalyst a compound of ruthenium.

* * * * *

UNITED STATES PATENT AND TRADEMARK OFFICE
CERTIFICATE OF CORRECTION

PATENT NO. : 5,026,904

DATED : June 25, 1991

INVENTOR(S) : PHILIP G. LODGE et al

It is certified that error appears in the above-identified patent and that said Letters Patent is hereby corrected as shown below:

Col. 3, l. 63, after with should read "$CO_2$ and then .... ."

Col. 6, l.7, after "a" should read "compound of an"

Signed and Sealed this

First Day of December, 1992

Attest:

DOUGLAS B. COMER

Attesting Officer     Acting Commissioner of Patents and Trademarks